United States Patent [19]

D'Andrea

[11] 4,303,066
[45] Dec. 1, 1981

[54] BURN DRESSING

[75] Inventor: Mark J. D'Andrea, Neshanic Station, N.J.

[73] Assignee: National Patent Development Corporation, New York, N.Y.

[21] Appl. No.: 52,924

[22] Filed: Jun. 28, 1979

[51] Int. Cl.³ .............................................. A61L 15/00
[52] U.S. Cl. ................................................. 128/156
[58] Field of Search ............................. 128/155–156; 424/DIG. 13, 7, 28, 31–33, 36

[56] References Cited

U.S. PATENT DOCUMENTS

| | | | |
|---|---|---|---|
| 3,220,960 | 11/1965 | Wichterle et al. | 128/156 |
| 3,577,516 | 5/1971 | Gould et al. | 424/28 |
| 3,579,628 | 5/1971 | Gander et al. | 424/28 |
| 3,669,103 | 6/1972 | Harper et al. | 128/156 |
| 3,963,685 | 6/1976 | Abrahams | 128/155 |
| 4,226,232 | 10/1980 | Spence | 128/156 |

Primary Examiner—C. Fred Rosenbaum
Attorney, Agent, or Firm—Cushman, Darby & Cushman

[57] ABSTRACT

A two package system useful in forming a rapid plastic film, i.e., a burn dressing or burn bandage, on the burn of the skin. One package contains particulate hydrophilic polymer such as 2-hydroxyethyl methacrylate polymer and the other package contains a liquid mixture of an inert, high boiling, organic liquid and water desirably in a weight ratio of 70:30 to 30:70. The particulate polymer and liquid mixture are desirably applied to the burn simultaneously, or by first applying the liquid mixture followed by application of the polymer. A plastic film, burn dressing, can result in a few minutes.

29 Claims, 1 Drawing Figure

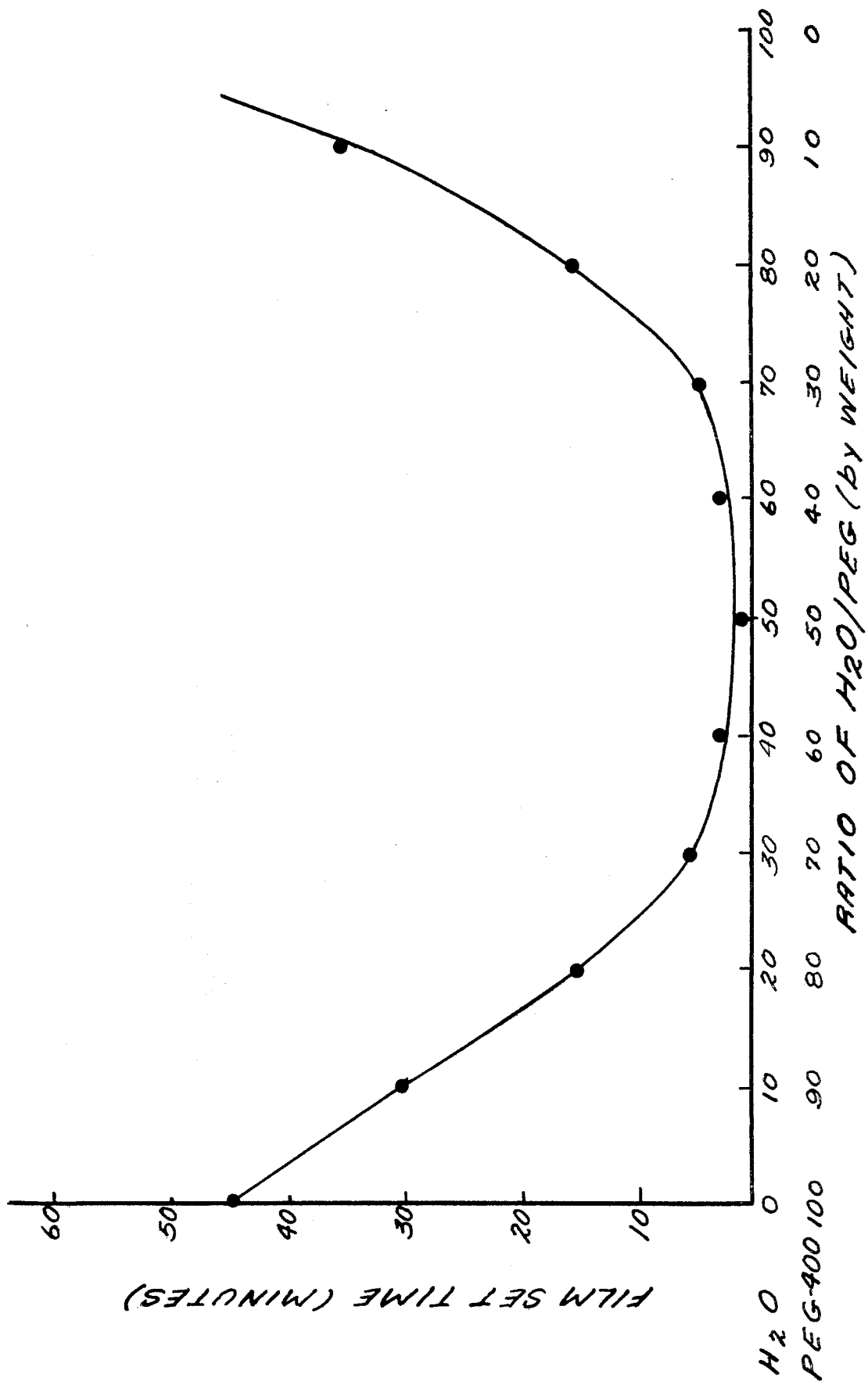

BURN DRESSING

BACKGROUND OF THE INVENTION

The present invention relates to improvements in the treatment of burns.

Thermal injuries require a unique combination of therapy and dressing as the physiologic functions of the skin are absent or, at best, materially impaired. Various proposals have been made to provide a film or protective barrier to the involved lesion including generally providing polymer compositions capable of forming in situ pinhole-free, mechanically strong, translucent or transparent or opaque, non-tacky dressing. Typically, such procedures include application of a normally liquid organic vehicle to the affected area followed by or simultaneously with a powdery hydrophilic polymer. The bandage or dressing thus being formed is a plastic film of hydrophilic polymer solvated into the liquid organic vehicle. Notwithstanding clinical acceptance of such dressing and technique, clinicians reported that the film set-up time, i.e., that amount of time from when the organic vehicle and hydrophilic polymer come into contact until the desired film burn dressing is achieved, was in many cases excessive, often taking as long as one hour, or longer. The set-up time is inconvenient, often painful, to the patient who must maintain the treated area in immobile condition. This is particularly true in instances of larger burn wounds.

BRIEF DESCRIPTION OF THE DRAWING

The drawing graphically illustrates film forming time in relation to the amount of PEC present.

DESCRIPTION OF THE INVENTION

It has now been discovered quite unexpectedly, indeed, that the film set time required from the application of the inert, normally liquid, organic vehicle and powdery hydrophilic polymer to form a burn dressing or film having good mechanical strength, integrity and adhesion to the skin can be significantly reduced by including in said organic vehicle a predetermined amount of water.

By the practice of the invention and its various embodiments a novel multipackage system, preferably a two package system, can be employed in the novel process to obtain such burn bandages or dressings (plastic film on the wound) in which the film set time is reduced to as low as a few minutes. Moreover, this feature of desirable set time is obtained while maintaining the necessary properties of good mechanical strength, integrity and film adhesion to the skin. The novel multipackage system comprises one package of particulate (powdery) hydrophilic polymer and a second package containing an inert, normally liquid organic liquid and water. Optionally, a portion of all of the water may be contained in a third package. If two packages of the novel multipackage system contain liquid components, then it is desirable to mix the liquid components together prior to application of the novel system to the skin (wound). For convenience, the novel multipackage system will be described herein with reference to a two package system.

One package of the novel two package system comprises particulate, water-insoluble, water-swellable, non-toxic, hydrophilic polymer. The hydrophilic polymer should be capable of forming with water a water-insoluble hydrogel and should also be soluble and/or solvatable in lower alkanols such as methyl alcohol, ethyl alcohol, isopropyl alcohol, isobutyl alcohol, and the like; aliphatic polyols such as glycols and polyglycols, e.g., ethylene glycol, propylene glycol, butylene glycol, diethylene glycol, triethylene glycol, and higher polyethylene glycols; the polypropylene glycols; the mixed polyoxyethylene-oxypropylene glycols; dimethyl sulfoxide; and the like. Especially noteworthy is the solubility or/and solvatability of the polymer in liquid glycols and polyoxyethyleneoxypropylene glycols of average molecular weights of at least 150, preferably at least 400, and upwards to a few thousand, e.g., about 2000, preferably about 800. The polymer can be soluble in water-alcohols mixtures, e.g., 95% methanol, but as stated above it should not be soluble in water alone. Desirably, the polymer has a high purity level (low level of residual monomer to prevent toxic or allergenic reaction). Also, desirably it should be water-insoluble or very sparingly water soluble to prevent excess tackiness caused be perspiration, liquid oozing from the wound, etc.

The molecular weight of the hydrophilic polymer desirably is above 50,000 and preferably above about 250,000 and upwards to several million. Molecular weights over the entire range and even outside these limits may be tolerated providing the hydrophilic polymers meet the characteristics noted in this specification. Desirably the polymer is micropulverized to particles of a dimension smaller than 50 mesh, preferably below 150 mesh (Tyler sieve). Desirably bulk density of the particulate hydrophilic powder is at least about 0.6 gram/cc, and preferably at least about 0.7 gram/cc, especially for polymers in the 100 to 375 mesh range, e.g., polymers of 2-hydroxyethyl methacrylate.

The second package of the novel two package system comprises an inert, non-toxic, normally-liquid, water-miscible organic liquid and water. The organic liquids which are useful in the practice of the invention are exemplified by water-miscible polar compounds including the glycols such as ethylene glycol, propylene glycol, butanediol-1,3, butanediol-1,4, hexanediol-2,5, 2-methyl-2,4-pentanediol, heptanediol-2,4, 2-ethyl-1,3-hexanediol, diethylene glycol, triethylene glycol, tetraethylene glycols, and the higher polyethylene glycols and other water-soluble oxyalkylene homopolymers and copolymers having a molecular weight up to 2000, and higher, desirably up to 1600, e.g., hydroxy-terminated polymers of ethylene oxide having average molecular weights of 200–1000, the water-soluble oxyethyleneoxypropylene polyol (especially glycol) polymers having molecular weights up to about 1500, desirably up to about 1000, propylene glycol monoethyl ether, monoacetin, tri(hydroxyethyl) citrate, ethylene glycol monomethyl ether, ethylene glycol monoethyl ether, di(hydroxypropyl) oxalate, hydroxypropyl acetate, glyceryl triacetate, glyceryl tributyrate, liquid sorbitol ethylene oxide adducts, liquid glycerine ethylene oxide adducts, diethylene glycol monomethyl ether, diethylene glycol monoethyl ether, and ethylene glycol diacetate.

The organic liquids have boiling points above 120° C., and preferably above about 200° C. The organic liquids vehicles which are particularly useful in forming non-tacky plastisol films when combined with the particulate hydrophilic polymer are those characterized by: (i) a plurality of oxyethylene ($-OCH_2-CH_2-$)

units in the molecule, and (ii) a boiling point above about 200° C.

The proportion of water to organic liquid in the second package of the novel multipackage system will be governed, to a noticeable extent, by variables such as the hydrophilic polymer of choice, the bulk density of the polymer, the molecular weight of the polymer, the organic liquid of choice, the molecular weight of the organic liquid, the particular film set time or range desired, and other factors. An amount of water in the range of 5 to about 95 weight percent, based on the total weight of water and organic liquid, has been shown to lower the film set time of the resulting burn dressing or film vis-a-vis the comparable system which does not employ water in the burn dressing formulation. As appears from FIG. 1, the results are somewhat more noticeable when the amount of water is increased to about 10 to 90 weight percent. However, it has been observed that above 80 weight percent water in the liquid package results in a burn dressing or film of poor integrity and insufficient mechanical adhesion that it will actually "lift off the skin". An amount of water in the range of about 10 to 80 weight percent is broadly suitable in most instances. At water concentrations of about 20 to 80 weight percent there is observed a noticeable decrease in the film set time while obtaining good mechanical strength, integrity and adhesion in the resulting film. An unexpected and obvious lowering of the film set time to within a narrow time range, e.g., a few minutes to less than 10 minutes, while obtaining a broad spectrum of highly desirable overall properties such as those discussed above, has been observed (as seen in FIG. 1) when the water concentration is from about 30 to about 70 weight percent, based on the total weight of the liquid package.

The concentration of particulate hydrophilic polymer to liquid is at least sufficient to form a non-tacky plastisol film on the skin. The weight ratio of particulate hydrophilic polymer to the total liquid components can range, for example, from 1:2 to 10:1, desirably 2:3 to 3:1, and preferably from 1:1 to 2:1, e.g., about 1.5 to 1.

According to one embodiment of the present invention, novel plastisol compositions can be prepared in situ as pinhole-free, mechanically strong, translucent or transparent or opaque, non-tacky, non-toxic, non-stinging, hydrophilic films, and which can be used advantageously to form occlusive dressings on the skin. Such dressings have proved particularly useful in the treatment of burn trauma.

Preferably, the liquid component is applied to the burn victim as a coating on the burn, e.g., by applying the organic vehicle to the burn patient, followed by application of the particulate polymer thereon, e.g., by nebulization (without a stinging propellant) onto such coating. In another desirable mode, the liquid component is applied simultaneously with the particulate polymer generally by atomization to the situs of the burn. Other methods of application are to direct a gentle stream of the liquid component to the burn area followed by application of the hydrophilic polymer and vice versa. There results a plastic film (which on a burn victim has been often-times referred to herein as a burn bandage or burn dressing) of hydrophilic polymer gel solvated into the liquid component (organic liquid and water). Any excess powdery polymer can be readily removed, e.g., brushing, dusting, etc. The film can be made transparent, translucent or otherwise. However, the finished bandage is removable by soaking in water.

It appears that in the in situ formation of the occlusive wound dressing the initial application of the solvating liquid component "wets" the surface of the wound as the liquid penetrates all the details of the eschar, such as by atomizing the liquid in small droplets, swabbing, or pouring according to the location or the appearance of the wound. As the hydrophilic powder is applied, the surface of the particles dissolves and the swollen particles adhere to each other to form a continuous film. Powder can be added until the liquid layer is saturated since excess powder remains dry and can be removed. Within a few minutes the film forms, in general, a translucent plastisol, the external surface of which appears dry to the touch, i.e., without excess liquid component. The film possesses good mechanical strength, integrity and adhesion to the skin. The film can remain in place as long as required by the progress of the healing process (up to a week or more). The dressing can be readily removed by bathing or washing with water, or by pulling.

The thickness of the in situ dressing can be adequately controlled by monitoring the quantities and rates of delivery of the two components. Good control is achieved by first controlling the thickness of the "initial" wetting of the wound, e.g., a thick layer of the solubilizing liquid component will tend to result in a thick dressing. Good control also is achieved by alternating the application of the particulate polymer and the solubilizing liquid component until a continuous, homogenous film over the wound area is obtained.

As the hydrophilic polymeric component useful in the practice of the inventions there is used a hydrophilic, water-insoluble, water-swellable, generally three dimensional, non-toxic, fine powdery solid. Preferred classes of monomers useful in the preparation of the hydrophilic polymer component are the hydroxyalkyl 2-alkenoates such as the hydroxy($C_1$–$C_4$alkyl) methacrylates and the hydroxy($C_1$–$C_4$alkyl) acrylates; the N-vinylpyrrolidones including the mono- and di-($C_1$–$C_4$alkyl)-N-vinylpyrrolidones: the 2-alkenamides including the N-($C_1$–$C_4$alkyl)-2-alkenamides and $N_1$N-di($C_1$–$C_4$-alkyl)-2-alkenamides such as the N-($C_1$–$C_4$alkyl)acrylamides, the N-($C_1$–$C_4$alkyl)-methacrylamides, the $N_1$N-di($C_1$–$C_4$alkyl)acrylamides, and $N_1$N-di($C_1$–$C_4$alkyl)methacrylamides; the vicinal-epoxyalkyl 2-alkenoates including the vicinal-epoxy($C_1$–$C_4$alkyl) methacrylates, and the vicinal-epoxy($C_1$–$C_4$alkyl) acrylates; with or without other monomers or modifiers such as the alkyl alkanoates; e.g., methyl butyrate, butyl acetate, etc.; the dialkylaminalkyl 2-alkenoates, e.g., diethylaminoethyl methacrylate; the vinylpyridines; the lower alkoxy(lower alkyl) methacrylates, e.g., ethoxyethyl methacrylate; and mixtures of the illustrative foregoing compounds.

Preferred monomers include, by way of examples, 2-hydroxyethyl acrylate, 2-hydroxyethyl methacrylate, diethylene glycol monoacrylate, diethylene glycol monomethacrylate, 2-hydropropyl acrylate, 2-hydroxypropyl methacrylate, 3-hydroxypropyl acrylate, 3-hydroxypropyl methacrylate, dipropylene glycol monomethacrylate, dipropylene glycol monoacrylate, acrylamide, N-methylmethacrylamide, N,N-dimethacrylamide, methylvinylpyrrolidone, glycidyl methacrylate, 2,3-dihydroxypropyl methacrylate, and the like. Most preferred is 2-hydroxyethyl methacrylate.

Desirably, small amounts of cross-linking agent or other ingredient either inherently contained in the monomer and/or added thereto, or other means, e.g., photopolymerization, can be employed to impart a three-dimensional structure to the resulting hydrophilic polymer.

Also contemplated in the practice of the invention are polymers such as the partially cross-linked polyethyleneimine, polyoxyethylene, vinylpyrrolidone polymers which are rendered insoluble in water; hydroxy lower alkyl cellulose polymers, cross-linked or otherwise, rendered insoluble in water but still retaining their hydrophilicity and solubility in organic solvents, e.g., from hydroxyethyl cellulose, hydroxy propyl cellulose, or carboxymethyl cellulose; partially cross-linked natural polymers such as guar gum, karaya gum, and salts of alginic acid which are rendered water insoluble but organic solvent soluble; and polyvinyl alcohol including the various partially hydrolyzed polyvinyl acetates.

Particularly suitable hydrophilic polymers are those which are characterized by at least 50 mol percent, preferably at least 80 mol percent, of the following recurring unit:

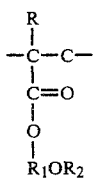

wherein R is hydrogen or methyl; wherein $R_1$ is $C_2$–$C_4$alkylene, e.g., ethylene, propylene or butylene; and wherein $R_2$ is hydrogen or $C_1$–$C_4$alkyl, or $C_1$–$C_4$alkoxy$C_1$–$C_4$alkyl.

The most preferred polymer for the present invention is a hydroxyethyl methacrylate polymer prepared by aqueous bulk polymerization using ultra-pure monomers characterized by a very low concentration of impurities conducive to crosslinking reactions, see U.S. Pat. No. 3,963,685. The above polymers can be prepared under "clean conditions" easily purified from residual monomers, and easily reduced to powders of the desired particle size.

It has also been determined that solvent-soluble conventional hydrogel forming polymers, e.g., as in U.S. Pat. No. 3,577,516 to Gould et al., U.S. Pat. No. 3,618,213 to Shepherd, and U.S. Pat. No. 3,575,946 to Chromacek, of sufficiently high molecular weight can be transformed into a hydrophilic polymer powder suitable for application as burn dressing powder component. This process involves first dissolving the polymers in a low boiling point solvent, preferably ethyl alcohol of high purity (at least USP), then filtering the resulting solution through a fritted glass filter (medium porosity). The filtered solution is then cast on clean surfaces and the solvent removed. The then dry film is then collected and ground to the appropriate mesh size. The entire disclosure of the aforesaid patents is hereby incorporated by reference.

If a hydrophilic monomer results in a polymer which is water soluble, e.g., polyacrylamide, it is necessary to employ up to 50 mol percent of a copolymerizable monomer to render it only water swellable, rather than water soluble. Such comonomers include, by way of illustrations, methyl acrylate, ethyl acrylate, propyl acrylate, butyl acrylate, 2-ethylhexyl acrylate, ethyl methacrylate, butyl methacrylate, methoxyethyl acrylate, methoxyethyl methacrylate, and ethoxyethyl methacrylate.

Furthermore, medicinally active ingredients such as germicides, fungicides, antibiotics, analgesics, or the like may be utilized by having the medicinally active ingredient suspended, entrapped in, or admixed with the polymer, or if desired dissolved in the liquid phase of the multipackage system. Examples of such medicinally active ingredients include silver sulfadiazine benzocaine, xylocaine, aspirin, sodium omadine (a derivative of 1-hydroxypyridine-2-thione), hexachlorophene, bacitracin, cortisone, trimethylbenzylammonium chloride, cetyl pyridinium chloride, penicillin, Aureomycin (chlorotetracycline), chloromycetin (chloromphenicol), merthiolate, sulfanilamide, sulfathiaozole, sulfaguanidine, sulfapyridine, salicylic acid, Griseofulvin, undecylenic acid, zinc undecylenate, tetracycline, hydroxytetracycline (Terramycin), silver nitrate, ascorbic acid.

The medicinally active ingredients can be incorporated into the dressing by one or more of the following procedures:

A. Incorporation in the hydrophilic powder by any of the processes described in U.S. Pat. No. 3,576,760, the entire disclosure of which is hereby incorporated by reference.

B. Incorporation with the liquid component by mixing the solubilizing component with the drug. The drug does not have to be soluble in the liquid.

C. Application of the drug on the wound before or during application of the hydrophilic polymer and/or liquid component.

D. Application of the drug on the surface of the occlusive dressing.

A particular advantage which is achieved in the practice of the novel method is the in situ formation of a plastic (film) dressing or bandage on the burned anatomy of a burn victim in which the film set-up time is substantially reduced to several minutes, e.g., less than 10-15 minutes in preferred embodiments. It appears that the film set-up time is directly influenced by the rate of solubilization of the powdery polymeric component in the inert organic liquid/water containing component, so that as the rate of powder polymer dissolution is increased the time required to produce an integrous film will be decreased. While not wishing to express any scientific theory, it appears that the water present in the liquid vehicle acts to swell the polymer chains thereby making the polymeric chains more accessible for solubilization by the inert organic liquid, thus the water present may tend to increase the polymer surface area in order that more polymeric chains may be solubilized. Such polymer swelling may also produce channels within the polymer.

The invention can be used to treat burns, particularly third and fourth degree burns on any skin surface, e.g., on the arms, legs, face, back, head or stomach. The invention is useful not only in treating humans, but also in veterinary medicine, e.g., to treat burns on dogs, cats, sheep, cattle, rabbits, guinea pigs, horses and zoological animals such as lions, tigers, deer, zebra, etc.

The synthetic film comprised of particulate hydrophilic polymer forms on the open surface of the burn and molds itself to the granulating wound.

Unless otherwise indicated, all parts and percentages are by weight. The liquid component was polyethylene glycol 400 (designated herein as PEG-400).

EXAMPLE 1

The particulate hydrophilic polymer prepared via an aqueous polymerization using 35 parts of 2-hydroxyethyl methacrylate (HEMA) which contained less than 0.04 part of ethylene glycol dimethacrylate. In one container ammonium persulfate (0.0875 part) was dissolved in 32.5 parts of purified water and in a second container sodium metabisulfite (0.0875 part) was dissolved in 32.5 parts of water. The HEMA and both aqueous solutions (redox system) were mixed together in a polyethylene bag which was closed by heat sealing. After 18 hours at room temperature, i.e., about 22° C., the resulting wet polymeric sponge was recovered, wet ground to particles sizes of about 2–4 mm. in diameter, and leached in purified water to yield particulate polymer containing less than 500 ppm (parts per million) of total residuals, e.g., unreacted monomer, redox residue, etc.

The particulate hydrophilic 2-hydroxyethyl methacrylate polymer was then dried, micropulverized and classified. This hydrophilic polymer possessed the following characteristics: soluble in methanol, water-swellable but not water soluble, bulk density of about 0.7 gm/cc, particle size distribution of $106\mu$–$45\mu$ with no more than 15 weight percent of the particles being less than $45\mu$ in diameter, and a reduced viscosity of about 2 dl/g (measured at 0.5 part polymer dissolved in 100 parts of 2-methoxyethanol at about 22° C.; Cannon-Fenske Viscometer 100).

Thereafter, ten sterilized two-package systems were prepared. In the ten systems the first package always contained the aforedescribed micropulverized polymer; the second package contained the liquid component as follows: (1) 100% PEG 400; (2) 90% PEG 400/10% water; (3) 80% PEG 400/20% water; (4) 70% PEG 400/30% water; (5) 60% PEG 400/40% water; (6) 50% PEG 400/50% water; (7) 40% PEG 400/60% water; (8) 30% PEG 400/70% water; (9) 20% PEG 400/80% water; and (10) 10% PEG 400/90% water.

The contents of the two-package system was then placed in separate reservoirs of a nitrogen spray applicator system (Hydron ® Burn Dressing Applicator Unit, DS-001). Application onto a shaved portion of a human forearm is as follows.

Hold the liquid dispenser about 6–12 inches from the surface and depress the thumb-plunger of the cut-off assembly. Apply a thin layer of liquid component on about 3"×4" area of the forearm. Use a steady back and forth motion to achieve uniformity and completeness of coverage. This layer should be kept thin, i.e., enough to wet the entire area to be covered, but without sites of fluid accumulation. Release the cut-off assembly thumb-plunger when the desired coverage is achieved.

Powder component should then be directed onto the layer of the liquid component, using a comparable technique with the powder component dispenser, until the resulting surface appears to be dry. A total of four alternating layers of liquid component and powder component are applied. After a period of time (film set time), there is obtained a plastic film having the characteristics described hereinabove.

Film set times were determined as follows. The length of time required to form a film of acceptable quality is judged by removing a small segment of the film (~1"×2") from the forearm after a certain post-application time and subjecting the specimen to flexion. The specimen is draped over the middle finger so as to cover the center knuckle and is manually held in place. The film is pressed firmly to the extended finger and the fingers flexed five times in as many seconds. The film is removed and visually inspected for any disturbances of integrity such as tears or stretch marks indicating inelastic stretching. For the purpose of determining film set times, a film is judged to be of acceptable quality if flexion has produced no tears or signs of inelastic stretching of the film. The resulting film contained about 55–60% powdery component and 45–40% of the liquid component. Film set time determinations were performed at ambient temperatures of about 22° C. and a relative humidity of about 60%. The film set times for the ten two-package systems are set forth in Table I below.

TABLE I

| Liquid Component | Film Set Time (Minutes) |
| --- | --- |
| 100 PEG 400 | 45 |
| 90 PEG 400/10 $H_2O$ | 30 |
| 80 PEG 400/20 $H_2O$ | 15 |
| 70 PEG 400/30 $H_2O$ | 5 |
| 60 PEG 400/40 $H_2O$ | 3 |
| 50 PEG 400/50 $H_2O$ | 1 |
| 40 PEG 400/60 $H_2O$ | 2 |
| 30 PEG 400/70 $H_2O$ | 4 |
| 20 PEG 400/80 $H_2O$ | 15 |
| 10 PEG 400/90 $H_2O$ | 35 |

The data in Table I above is graphically depicted in FIG. 1.

EXAMPLE 2

The procedure of Example 1 was repeated with six two-package systems in which the powder component (of Example 1) is the same in each system and the liquid component comprised the following composition: (1) 100% PEG-400; (2) 90% PEG-400/10% $H_2O$; (3) 80% PEG-400/20% $H_2O$; (4) 70% PEG-400/30% $H_2O$; (5) 60% PEG-400/40% $H_2O$; and (6) 50% PEG-400/50% $H_2O$. Film set time determinations were performed at ambient temperatures of about 22° C. and a relative humidity of about 45%. The film set times for the six two-package systems are set forth in Table II below.

TABLE II

| Liquid Component | Film Set Time (Minutes) |
| --- | --- |
| 100 PEG 400 | 60 |
| 90 PEG 400/10 $H_2O$ | 45 |
| 80 PEG 400/20 $H_2O$ | 35 |
| 70 PEG 400/30 $H_2O$ | 15 |
| 60 PEG 400/40 $H_2O$ | 10 |
| 50 PEG 400/50 $H_2O$ | 8 |

EXAMPLE 3

The objective of this Example is to provide quantitative comparative data on the mechanical properties of films prepared with PEG-400/water solutions and films made with 100% PEG-400. Mechanical film property data is important since, from a clinical point of view, a desirable product will allow good patient mobility and yet be mechanically strong enough to minimize or eliminate cracks from developing during normal use as a wound dressing.

Film samples were prepared using the spray applicator system of Example 1. The powder component of Example 1 was employed in all five two-package systems used in this example. The liquid component comprised (1) 100% PEG-400; (2) 80% PEG-400/20%

H₂O; (3) 70% PEG-400/30% H₂O; (4) 66% PEG-400/34% H₂O; and (5) 62% PEG-400/38% H₂O.

Starting at the upper left hand corner of a flat plate (12"×12"), spraying of the liquid component was started and the atomizer moved slowly to the right until the spray lightly coated an entire tract from left to right. Upon reaching the right hand corner of the plate, the atomizer was moved down to the next line of spray without interruption and continued, this time from right to left until this line of spray had been completed. Again, without interruption of the spray, the atomizer was moved down to the next line of spray. The oscillating movement of the atomizer was continued until the entire plate was lightly covered with the liquid component. The spraying was also done with the plates laying flat on a table top.

The second layer was applied using the bulk classified powder component. Altogether, 5 alternating layers of the liquid component and 5 layers of the powder component were applied to the plate using the same method of application as that described in the above paragraph.

All the films were applied on the same day in a room with a recorded temperature of 26° C. and relative humidity of 40%. Each plate was allowed to set in the air for 30 minutes after application of the spray. Each plate was double wrapped and sealed in polyethylene bags and stored in the room in which they were made for two days. After two days, the resulting film was prepared into test specimens in the following manner: The film was carefully peeled from the plate and layed on release paper. Using a mallet, six specimens were die cut. The die cut specimens were sandwiched between release paper and immediately heat sealed inside gas impermeable aluminum pouches. The specimens were then stored for three days at room temperature.

Table III infra contains the pertinent data relating to the mechanical strength of the films at ambient temperature (27° C.±1° C.) and ambient relative humidity (60%+1%). Each value represents an average of a minimum of five samples tested.

Each time a sample was run on the Instron, a graphical plot was obtained which enabled the calculation of the following parameters:

1. Tensile Strength at Break is the maximum tensile stress (i.e., applied force per unit of original cross sectioned area of a specimen) applied during stretching a specimen to rupture.

2. Ultimate Elongation is the maximum extension of a uniform section of a specimen prior to rupture produced by a tensile force applied to the specimen and is expressed as a percentage of the original length of the section.

3. Elastic Modulus is the ratio of stress (nominal) to corresponding strain below the proportional limit of the material and is expressed in force per unit area (i.e., psi).

4. Tensile Set at Break is the extension remaining after a specimen has been stretched to the point of rupture and allowed to retract in a specified manner. It is expressed as a percentage of the original length.

TABLE III

| PEG-400/H₂O | Tensile Strength at Break (psi) | Ultimate Elongation (%) | Elastic Modulus (psi) | Tension Set at Break (%) |
|---|---|---|---|---|
| 100/0 (Control) | 16 | 565 | 349 | 4 |
| 80/20 | 21 | 319 | 548 | 8 |
| 70/30 | 20 | 258 | 548 | 0 |
| 66/34 | 19 | 534 | 378 | 0 |
| 62/38 | 14 | 412 | 338 | 4 |

When interpreting the above data it will be appreciated that although every effort was made to prepare identical specimen films, the mode of application of the liquid and powder components make exact duplicates difficult.

The results show that all the films, whether made with 100% PEG-400 or PEG-400/water solutions are readily deformable and pliant which are characteristics desired in a viable burn or wound covering.

The modulus of elasticity is an expression of the relationship of the stress to the strain—an indicator of how much force is required to produce a given deformation. A material with a low elastic modulus is easily deformed. Assuming the strength of the bond between the dressing and the burn wound is small, a material with a low elastic modulus is desired so that the interfacial bond is not destroyed as a result of patient movement. The ultimate elongation represents the degree to which a material can be stretched at break. Since several areas on the body are routinely subject to flexion, a material with a high percentage of ultimate elongation is desired. Also, a material with a low amount of extension remaining after it has been stretched (i.e., low tension set) is necessary since once the material has been stretched, as in the bending of an elbow, the interfacial bond between the wound and the dressing will not be disturbed.

A low modulus of elasticity, a high ultimate elongation and a low tension set are all properties desired in a burn dressing. Such properties have been adequately achieved by the PEG-400/water formulations tested and are thus mechanically substantially equivalent to those formulations based on 100% PEG-400.

The above evidence indicates that it is fully possible to reduce the film set-up time of a two component hydrophilic polymeric burn dressing by the addition of an appropriate amount of water. Film set-up times may thus be reduced from one hour down to a period of about 10 minutes and less. From the clinical viewpoint this decrease in film set-up time means that the patient need remain immobile for much less time, thereby contributing to the patient's overall comfort. In addition, as the film set-up time is decreased, e.g., to 15–20 minutes, there will be less chance for disruptment of the dressing due to patient movement, thus avoiding repairs that are necessitated by products having a longer set-up time.

What is claimed is:

1. A two-package system useful in forming a non-tacky, non-toxic, non-stinging plastic burn dressing directly on the wound of the skin which consists essentially of:

(a) a first package containing particulate hydrophilic polymer having the following characteristics: lower-alkanol insolubility, water-swellability, water-insolubility, and a molecular weight above about 50,000; and (b) a second package used with said first package and containing liquid comprised of from 20 to 80 weight percent water and from 80 to 20 weight percent of an inert organic liquid, said organic liquid being characterized by a boiling point of at least about 120° C. and water-miscibility.

2. The two-package system of claim 1 wherein the concentration of particulate hydrophilic polymer to liquid is at least sufficient to form a non-tacky plastisol film onto the skin; wherein said polymer is characterized by at least 50 mol percent of the following recurring unit:

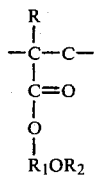

wherein R is hydrogen or methyl, wherein $R_1$ is $C_2$-$C_4$alkylene, and wherein $R_2$ is hydrogen, $C_1$-$C_4$alkyl or $C_1$-$C_4$alkoxy$C_1$-$C_4$alkyl; and wherein said organic liquid is a glycol.

3. The two-package system of claim 2 wherein said polymer is characterized by a bulk density of at least about 0.6 gram/cc and wherein said organic liquid is characterized by a plurality of oxyethylene units in the molecule and a boiling point of at least about 200° C.

4. The two-package system of claim 3 wherein said polymer is characterized by at least 80 mol percent of the recurring unit and wherein the organic liquid is a oxyethylene polymer having a molecular weight up to 2000.

5. The two-package system of claim 2 wherein said second package contains a liquid comprised of from 30 to 70 weight percent water and from 70 to 30 weight percent inert organic liquid.

6. The two-package system of claim 4 wherein said polymer is a polymer of 2-hydroxyethyl methacrylate and wherein said organic liquid is polyethylene glycol.

7. The two-package system of claim 6 wherein said second package contains a liquid comprised of from 30 to 70 weight percent water and from 70 to 30 weight percent inert organic liquid.

8. The two-package system of claim 7 wherein said organic liquid is polyethylene glycol having a molecular weight of 150 to 800.

9. The two-package system of claim 8 wherein said organic liquid is polyethylene glycol having a molecular weight of about 400 and wherein said polymer is a three-dimensional poly(2-hydroxyethyl methacrylate).

10. A non-tacky, non-irritating, innocuous, non-stinging, pinhole-free burn dressing which comprises a plastisol formed by contacting a liquid comprised of 20 to 80 weight percent water and 80 to 20 weight percent organic vehicle which (i) is non-toxic and (ii) is characterized by a boiling point of at least about 120° C.; with a particulate hydrophilic polymer characterized by (i) lower-alkanol solubility, (ii) water-insolubility, (iii) water-swellability, and (iv) an average molecular weight of at least about 50,000; the concentration of said polymer to said vehicle being at least sufficient to form a non-tacky plastisol.

11. The burn dressing of claim 10 wherein said liquid organic vehicle is characterized by a boiling point above about 200° C. and a plurality of oxyethylene units in the molecule; and wherein said polymer is a polymer of a hydroxy lower alkyl acrylate or methacrylate, of a hydroxy lower alkoxy lower alkyl acrylate or methacrylate, of acrylamide, of methacrylamide, of a N-lower alkylacrylamide or methacrylamide, of N,N-di-lower alkylacrylamide or methacrylamide, or of an N-vinylpyrrolidone.

12. The burn dressing of claim 11 wherein said liquid comprises 30 to 70 weight percent water and 70 to 30 weight percent organic vehicle which is a polyethylene glycol having an average molecular weight up to about 800, and wherein said particulate polymer is a polymer of 2-hydroxyethyl methacrylate.

13. The burn dressing of claim 12 wherein said particulate polymer has an average molecular weight greater than 250,000 and a bulk density of at least about 0.6 gram/cc.

14. In combination, a burned tissue surface and in contact therewith a non-tacky, non-irritating, innocuous, non-stinging, pinhole-free burn dressing therefor, said burn dressing comprising a plastisol formed by contacting a liquid comprised of 20 to 80 weight percent water and 80 to 20 weight percent organic vehicle which (i) is non-toxic and (ii) is characterized by a boiling point of at least about 120° C.; with a particulate hydrophilic polymer characterized by (i) lower-alkanol solubility, (ii) water-insolubility, (iii) water-swellability, and (iv) an average molecular weight of at least about 50,000; the concentration of said polymer to said vehicle being at least sufficient to form a non-tacky plastisol.

15. The combination of claim 14 wherein said liquid organic vehicle is characterized by a boiling point above about 200° C. and a plurality of oxyethylene units in the molecule; and wherein said polymer is characterized by a bulk density of at least about 0.6 gram/cc; the concentration of said polymer to said vehicle being in the range of from about 2:3 to about 3:1 by weight.

16. The combination of claim 15 wherein said liquid comprises 30 to 70 weight percent water and 70 to 30 weight percent organic vehicle which is a polyethylene glycol having an average molecular weight up to about 800, wherein said particulate polymer is a polymer of 2-hydroxyethyl methacrylate and wherein the weight ratio of said polymer to said liquid is in the range of from about 1:1 to about 2:1.

17. A process of treating a burned tissue surface comprising applying to the burned surface (1) a liquid comprised of 20 to 80 weight percent water and 80 to 20 weight percent organic liquid which (i) is non-toxic and (ii) is characterized by a boiling point of at least about 120° C.; (2) a particulate hydrophilic polymer characterized by (i) lower-alkanol solubility (ii) water-insolubility, (iii) water-swellability, and (iv) a moecular weight of at least about 50,000; allowing said liquid vehicle to solvate said polymer in situ on the burned surface to form a gelled, non-tacky, innocuous, non-stinging, plastisol burn dressing which prevents infection of the burn by microorganisms; (3) the weight ratio of said polymer to said liquid which forms the burning dressing being from 2:3 to 3:1.

18. The process according to claim 17 wherein (1) and (2) are applied substantially simultaneously to the debrided burned surface.

19. The process according to claim 17 wherein said liquid is applied first to the burn surface and then said polymer is applied on the liquid coating and is allowed to solvate to form a film.

20. The process according to claim 17 wherein the burn surface is of at least the debrided condition of a second degree burn.

21. The process according to claim 17 wherein said liquid organic vehicle is characterized by a boiling point above about 200° C. and a plurality of oxyethylene units in the molecule; and wherein said polymer is characterized by a bulk density of at least about 0.6 gram/cc; the weight ratio of said polymer to said vehicle being in the range of from about 1:1 to about 2:1 by weight.

22. The process according to claim 21 wherein said liquid organic vehicle is polyethylene glycol having an average molecular weight up to about 800, and said particulate polymer is a polymer of 2-hydroxyethyl methacrylate.

23. The process according to claim 22 wherein said particulate polymer has an average molecular weight greater than 250,000 and a bulk density of at least about 0.7 gram/cc.

24. A process of treating a debrided burned tissue surface consisting essentially of applying to said debrided burned surface the liquid and hydrophilic polymer of claim 22 and allowing the liquid to solvate said polymer in situ on the burned surface to form a gelled burn dressing which prevents infection of the burn by microorganisms.

25. A burn dressing consisting essentially of the composition of claim 24.

26. The process of claim 17 wherein (1) and (2) are applied to the surface of a burn ranging from a third degree burn to a fourth degree burn.

27. The process of claim 26 wherein the burn is a third degree burn.

28. The process of claim 21 wherein the burned surface is a burn ranging from a third degree burn to a fourth degree burn.

29. The process of claim 17 wherein the vehicle is polyethylene glycol molecular weight about 400 and the polymer is a three-dimensional polymer of 2-hydroxyethyl methacrylate having a bulk density at least about 0.6 gram/cc.

* * * * *

UNITED STATES PATENT AND TRADEMARK OFFICE
CERTIFICATE OF CORRECTION

PATENT NO. : 4,303,066
DATED : December 1, 1981
INVENTOR(S) : Mark J. D'Andrea

It is certified that error appears in the above—identified patent and that said Letters Patent is hereby corrected as shown below:

Column 10, Claim 1, lines 61-62, change "lower-alkanol insolubility" to --lower-alkanol solubility--.

Signed and Sealed this

Thirty-first Day of August 1982

[SEAL]

Attest:

GERALD J. MOSSINGHOFF

Attesting Officer

Commissioner of Patents and Trademarks